US000001324H

United States Statutory Invention Registration [19]

[11] Reg. Number: H1324

Dalke et al.

[43] Published: Jun. 7, 1994

[54] EXTRACORPOREAL CIRCULATION SYSTEM

[75] Inventors: William D. Dalke, Aurora; Gary A. Gruszecki, Arvada; Bruce Ellingboe, Littleton, all of Colo.

[73] Assignee: COBE Laboratories, Inc., Lakewood, Colo.

[21] Appl. No.: 941,389

[22] Filed: Sep. 8, 1992

[51] Int. Cl.[5] ..... A61M 31/00

[52] U.S. Cl. ..... 604/65; 128/DIG. 3; 128/DIG. 12; 128/DIG. 13; 604/66

[58] Field of Search ..... 604/65-67

[56] References Cited

PUBLICATIONS

"Perfusion Control System" by COBE, dated May 1991 (enclosed).

"Computerized Perfusion Controller Operator's Manual" by COBE Laboratories, Inc., dated Feb 1989 (enclosed).

"Precision Blood Pump Operator's Manual" by COBE Laboratories, Inc., dated 1985 (enclosed).

"We Gave the Heart and Lung a Brain" by Stockert/-Schiley, dated 1987 (enclosed).

"Aries Medical Model 2100 Centrifugal Pump System Operator's Manual Preliminary Copy" by Aries Medical, dated Mar. 24, 1990 (enclosed).

"The New Standard in Centrifugal Form and Function" by Aries Medical, undated (enclosed).

*Primary Examiner*—David H. Brown

*Attorney, Agent, or Firm*—Beaton & Swanson

[57] ABSTRACT

A system for controlling and monitoring the extracorporeal circulation of fluids, which is particularly useful in controlling and monitoring the circulation of blood and cardioplegia solution in surgical procedures. A set of perfusion assemblies are mounted in a transportable console, each perfusion assembly having a separable pump and control module pod. Virtually all the instrumentation for the monitoring and controlling of the pump and the fluid being pumped by that perfusion assembly are present on the pump and control module pod for that perfusion assembly, without the need for any separate control screen. Further, the perfusion assembly uses removable circuit cards and associated instrumentation strips to custom configure the perfusion assembly for each application. The perfusion assembly thereby provides complete information at a glance and complete control of the perfusion assembly by using dedicated controls that are grouped to each perfusion assembly. It is flexible in being configured to the desires of the user, is easy to use and involves a minimum of clutter.

55 Claims, 6 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

EXTRACORPOREAL CIRCULATION SYSTEM

FIELD OF THE INVENTION

The present invention relates to a system for the extracorporeal circulation of blood or blood components or other fluid through one or more pumps or other devices. The system has particular applicability to procedures for the extracorporeal circulation of blood and fluids in connection with open-heart surgery.

BACKGROUND OF THE INVENTION

Various forms of open-heart surgery have been practiced for a number of years. Open-heart surgery normally requires the use of a system for the extracorporeal circulation of fluids through a number of fluid circuits. For example, one circuit is used to assume the cardiopulmonary functions of the patient by bypassing the heart and lungs. In this circuit, a catheter receives blood from a major vessel entering the heart and directs the blood through a venous line to a blood reservoir. An arterial pump is used to pump blood from the reservoir through an oxygenation device such as a membrane or bubble oxygenator and through an arterial line and another catheter into a major vessel exiting the heart. This pumping and oxygenation function temporarily replaces or supplements the pumping and oxygenation function of the heart and lungs. The arterial pump circuit may include other devices such as bubble detectors to guard against bubbles entering the bloodstream; temperature sensors and heat exchangers to monitor and control the temperature of the circulated blood; pressure transducers to monitor the pressure in the extracorporeal circuit; a timer; cardiac index monitor; and devices to monitor blood characteristics such as the hemoglobin oxygen saturation level, hematocrit, pH, and blood gasses.

The arterial pump is typically a peristaltic pump in which a set of rollers are mounted on a rotor which rotates through a raceway. A flexible tube is mounted in the raceway between the raceway and the rollers. The rotation of the rotor moves the rollers through the raceway to successively occlude the flexible tube, thereby driving the fluid in the tube through the tube in the direction of the moving rollers. Rotary peristaltic pumps are attractive for pumping blood or other body fluids because they are relatively reliable and simple to operate, and they are sanitary since they do not directly contact the fluid being pumped. Centrifugal pumps or other types of pumps may also be used. Regardless of the type of pump that is used, it may be operated in a steady and continuous manner or in a pulsatile manner to mimic the beating of the heart.

Another potential circuit in the extracorporeal circulation system involves a cardioplegia pump. Most types of common surgery on the heart necessitate a temporary reduction or discontinuance in the beating of the heart in a manner that will not cause damage to the myocardium. This is accomplished by using a cardioplegia pump to pump a cardioplegia solution into the coronary arterial network for distribution throughout the myocardium. The solution drains through the coronary sinus, and can be drawn out of the chest cavity and discarded or directed toward the arterial pump for mixing with systemic blood.

The cardioplegia pump which infuses the myocardium arterial network with cardioplegia solution is typically somewhat similar in design to the arterial pump which bypasses the heart and lungs; it is commonly a peristaltic pump in which a set of rollers mounted on a rotating rotor successively occlude a flexible tube to drive the solution therethrough. As in the case of the arterial pump, the cardioplegia circuit may include other devices such as pressure transducers to monitor the solution pressure to keep it within an acceptable range; an air detector; a timer; and a temperature sensor and heat exchanger to monitor and control the temperature of the cardioplegia solution. In addition, the cardioplegia circuit may include a device for controlling and recording the total volume of cardioplegia solution that is pumped.

Typical extracorporeal systems for use in openheart surgery may contain one or more additional circuits, beyond the arterial circuit and cardioplegia circuit. For example, the system may include one or more auxiliary pumps to draw free blood and cardioplegia fluid from the patient and to add it to the blood reservoir to be mixed with systemic blood to be pumped by the arterial pump. Although uncommon, the system in some configurations may include a venous pump separate from the arterial pump to draw venous blood out of the patient and direct it to a reservoir where the arterial pump can pump it through an oxygenator and heat exchanger. One or more additional pumps may be included in the system for use as back-up pumps in the event of a failure of a primary pump.

Existing systems for extracorporeal circulation are commonly mounted on a wheeled console for convenient storage, transport and use. The typical mounting configuration includes a row of discrete perfusion assemblies, each perfusion assembly including a pump for use as an arterial pump, cardioplegia pump, auxiliary pump, back-up pump, or any other pump needed for the chosen system configuration. Each perfusion assembly may also include a pump control panel. The pump houses the actual pumping elements such as a rotor with a set of rollers to engage the flexible tubing through which the pumped fluid flows and a raceway to hold the flexible tubing in place. It also contains the pump motor and other mechanical components. The pump control panel may include controls such as power switches, speed adjustments and indicators, and forward and reverse controls.

The wheeled console commonly has a number of accessories and a structure for attachment of the accessories. The structure may include one or more vertical poles or "masts," a horizontal crossbar connecting one or more of the masts, and sets of hooks and brackets for hanging or attaching fluid reservoirs, accessory instrumentation, writing surfaces and any other desired elements such as bubble detectors, temperature sensor readouts and other devices mentioned previously.

In the prior art, the pump control panel for each perfusion assembly does not always include all the instrumentation associated with that perfusion assembly and the fluid being pumped by that perfusion assembly. Instead, the configuration generally used in the prior art involves positioning some of the instrumentation on the pump control panel and positioning other instrumentation on a separate module. For example, in one common configuration instrumentation such as speed control, delivery rate readout, forward and reverse, and certain other elements are positioned on the pump control panel for each pump, but other instrumentation such as pulsatile control, pressure detection, temperature readouts and certain other elements are positioned at a remote location. The remote location is often a central CRT, a conglomeration of modules or a touchscreen display module, that is used to control and display certain functions for all of the perfusion assemblies used in the system. This centralized display module is usually the source of more information and controls than can actually be displayed and operated at one time; therefore, the perfusionist must affirmatively request the information and controls that are to be displayed and operated from time to time.

The centralized display module is often mounted on one of the vertical masts attached to the console or to a horizontal crossbar that extends between two masts. It may share the masts and crossbar with pressure sensors, an oxygenator and reservoir, air bubble detectors, heat exchangers, individual instruments, and other accessories, all of which are suspended or attached to the structure by hooks and brackets.

SUMMARY OF THE INVENTION

The present invention includes a system for the extracorporeal circulation of blood or blood components or other fluid through several circuits using a plurality of perfusion assemblies. The invention conveniently and efficiently groups most of the therapeutic functions of each perfusion assembly and the fluid being pumped by that perfusion assembly at the perfusion assembly location, so that the operator can determine information and control parameters at a glance at a single location. Further, the perfusion assemblies and their instrumentation are designed to be very flexible in configuration and use, as explained in detail below. Finally, the system is designed to rely on dedicated controls so that not only can information and control parameters be determined at a glance, they can generally be determined without the need to affirmatively request them.

Each perfusion assembly is modular in design, with a detachable pump and control module pod. The detachability aspect of the pump and control module pod makes it easy and convenient to replace an element in case of a failure, even during a surgical procedure or during routine maintenance. These two elements attach and detach from one another by means of suitable mechanisms and are in electrical communication with one another through appropriate electrical connectors such as electrical cables with plugs and jacks.

The perfusion assembly contains virtually all the instrumentation that is pertinent to that perfusion assembly and the fluid being pumped by that perfusion assembly. In contrast with the typical prior art system, there is preferably no remote or separate display module for some of the instrumentation associated with a given perfusion assembly (although a remote module could also be used). Therefore, there is no need for the perfusionist to divide attention between two different monitor and control systems for one perfusion assembly and its pumped fluid. Instrumentation that may be present in a perfusion assembly includes devices to monitor and/or control the pumping rate; the pressure of the fluid being pumped; level/bubble indicators (to indicate a declining fluid level in a reservoir or the presence of air in the pumped fluid); the oxygen saturation level and hematocrit of blood being pumped; the pulsation parameters of the pump; timers; the temperature of the fluid being pumped; the volume of pumped fluid; the cardiac index; and anything else desired by the perfusionist and for which an appropriate sensor and input is provided.

Individual categories of instrumentation are in modular form within each perfusion assembly, preferably by means of individual circuit cards that are readily plugged or unplugged from the perfusion assembly. In addition, the control module pod of the perfusion assembly is designed to accept a number of removable and replaceable instrumentation strips corresponding to the circuit cards. For example, a perfusion assembly that is configured for use as an arterial pump may contain a plugged-in circuit card for use with appropriate sensors external to the perfusion assembly to process signals indicative of oxygen saturation levels and hematocrit of the pumped blood. Associated with the plugged-in circuit card would be a removable instrumentation strip for attachment to the control module pod, with suitable displays for saturation and hematocrit.

A perfusion assembly configured for use as a cardioplegia pump would not normally use the circuit card that processes saturation or hematocrit since those are not functions typically used in cardioplegia. However, the cardioplegia perfusion assembly may contain some other plugged in circuit card and associated instrumentation strip that is useful in a cardioplegia perfusion assembly but not in an arterial perfusion assembly, such as a circuit card and associated instrumentation strip to control and/or monitor the volume of fluid pumped. The plugged-in circuit card processes signals indicative of volume from feedback from the pump, and the corresponding instrumentation strip for attachment to the control module pod has appropriate controls and displays for programming and indicating volume information such as total delivered volume of cardioplegia fluid.

Other functions may be essentially the same for an arterial perfusion assembly and a cardioplegia perfusion assembly such as the level/bubble detector and pressure functions. In the case of functions that are the same between two perfusion assemblies, the circuit cards and associated instrumentation strips used in the two perfusion assemblies would be the same but, of course, the circuit card for the arterial perfusion assembly would be connected to a sensor associated with the arterial circuit while the circuit card for the cardioplegia perfusion assembly would be connected to a sensor associated with the cardioplegia circuit.

DETAILED DESCRIPTION OF THE INVENTION

Figure 1:
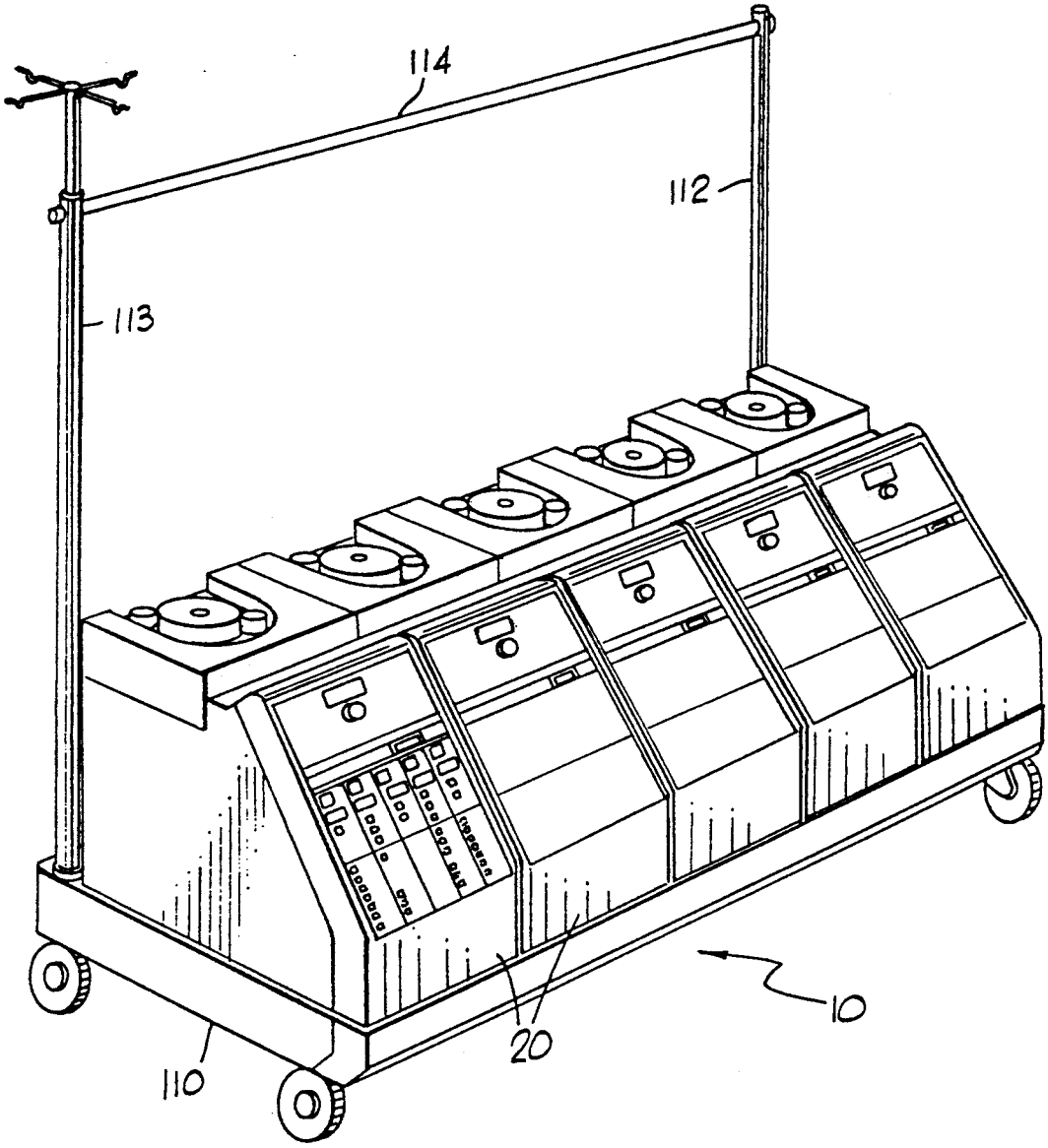
FIG. 1 is a pictorial view of a set of perfusion assemblies on a console in accordance with the present invention.

An overall pictorial view of a system 10 for perfusion is shown in FIG. 1, including a set of perfusion assemblies 20, a console 110 with suitable mounting fixtures such as masts 112 and 113 and a crossbar 114 for mounting an oxygenator and other accessories (not shown). The perfusion assemblies that are used for given procedures, of course, engage appropriate tubing sets which are not depicted in the figures.

A single perfusion assembly 20 is shown in several views in FIGS. 2–6. The perfusion assembly 20 includes a pump 24 and a control module pod 28. The pump 24 includes a pump head 32, a pump control panel 33 and a housing 30 which encloses a suitable drive mechanism. Briefly, the pump head may be of the peristaltic type in which a set of rollers are mounted on several arms of a rotor positioned in a raceway. Flexible tubing is placed between the raceway and the rollers so that the rollers engage the tubing to partially or fully occlude the tubing. The rotor is rotated at an adjustable rotational speed by the drive mechanism contained within the housing to move the rollers along the tubing, thereby driving fluid through the tubing. Ordinary peristaltic pump mechanisms and their drive mechanisms are well known in the art and are not further described here.

Figure 3:
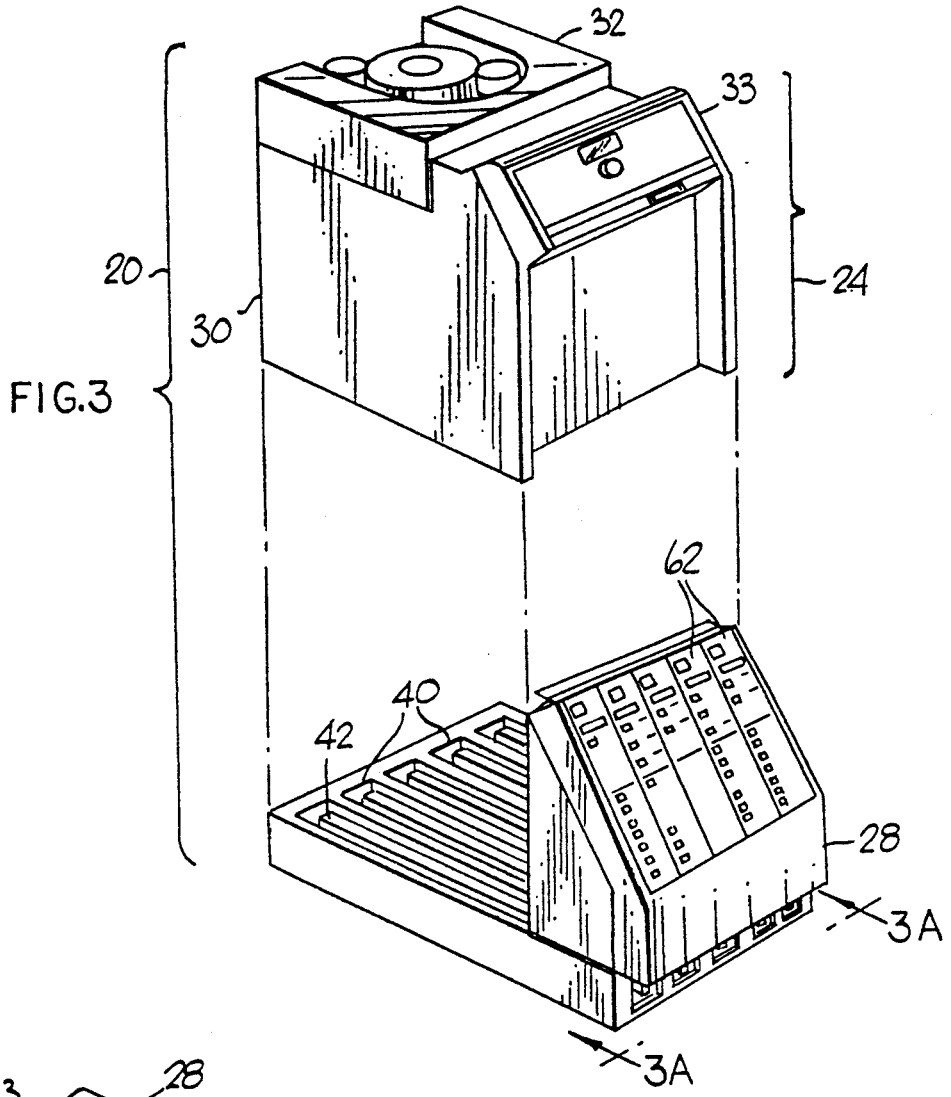
FIG. 3 is a pictorial view of a single perfusion assembly with the pump and control module pod separated.

The control module pod 28 and pump 24 of the perfusion assembly 20 are detachable in the manner shown in FIG. 3. The mechanical connection between the control module pod and the pump is accomplished with a suitable attachment system. The necessary electrical communication between the control module pod and the pump is accomplished with a set of cables with mating jacks and plugs or with any other satisfactory arrangement.

Figure 3A:
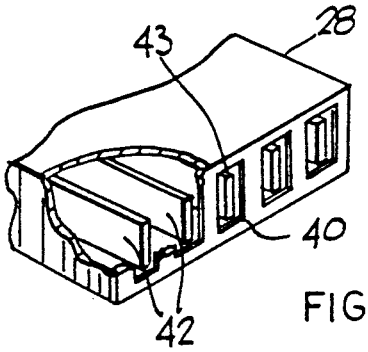
FIG. 3A is a perspective and partial sectional view of the control module pod of the perfusion assembly showing the circuit cards installed in the control module pod.

The control module pod 28 has a set of card slots 40 to receive circuit cards 42. The card slots are appropriately sized in relation to the circuit cards 42 so that the circuit card is free to slide into and out of the slot. The circuit card 42 may include a plug with a set of prongs that mate with a jack (not shown) in the card slot 40, in order to establish an electrical connection between the circuit card 42 and the control module 28. The exact locations of the card slots are not critical to the function of the machine but preferably they are in a location that is easily accessible by the manufacturer or service person. The plug and jack of each circuit card and card slot may also perform the function of holding the circuit card into the slot, or there may be other appropriate attachment devices for performing that function. A field connection slot 43 permits access to the circuit cards 42 as shown in FIG. 3A for connection of sensors to the circuit cards 42.

Each circuit card 42 contains circuitry necessary to process signals representative of a given function and transmit them to a microprocessor (not shown) for further processing. As used herein the processing of signals includes, without limitation, the conveying of unaltered signals to the microprocessor as well as various processes that alter or interpret the signal. For example, a pressure circuit card contains the circuitry necessary to receive signals from a pressure sensor, to process those signals in conjunction with the microprocessor to determine a fluid pressure, to transmit a signal indicative of the determined pressure to an appropriate site on the control module pod for translation into a display in the manner described below, and to process various pressure control information that is entered or requested by the operator.

Figure 2:
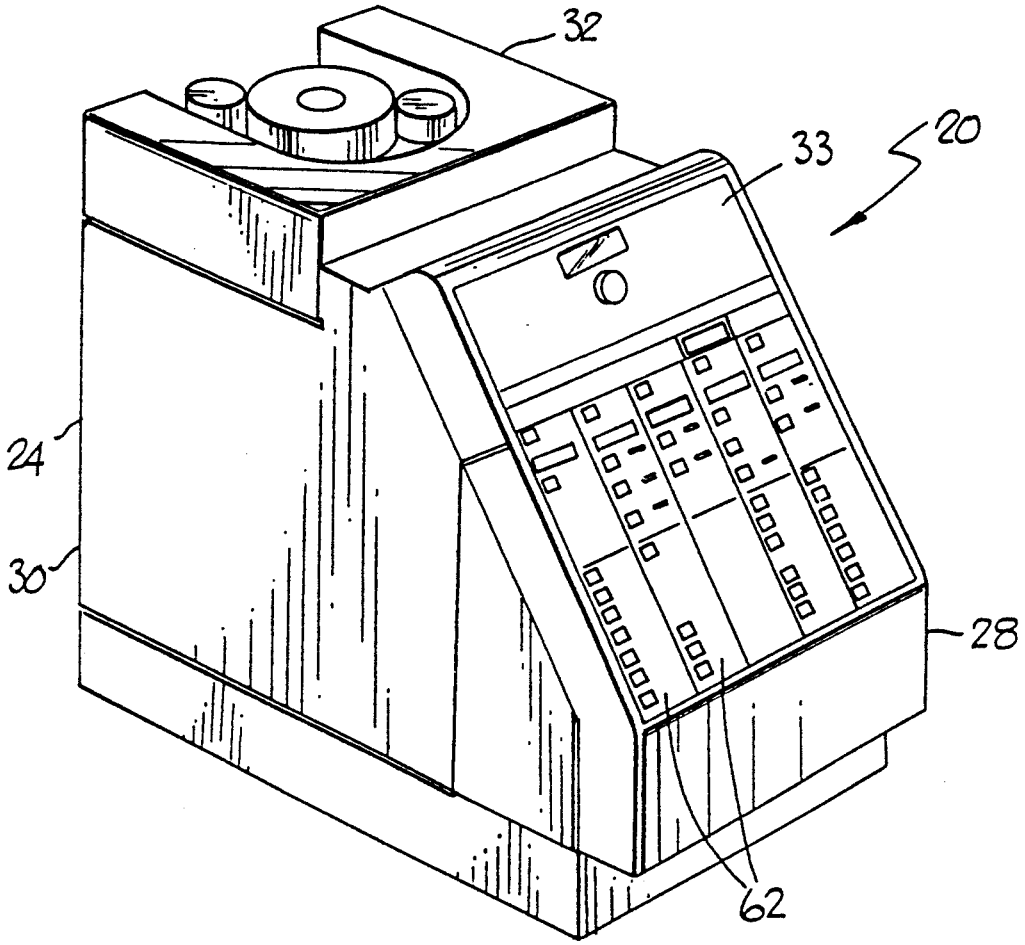
FIG. 2 is a pictorial view of a single perfusion assembly in accordance with the present invention.
Figure 4:
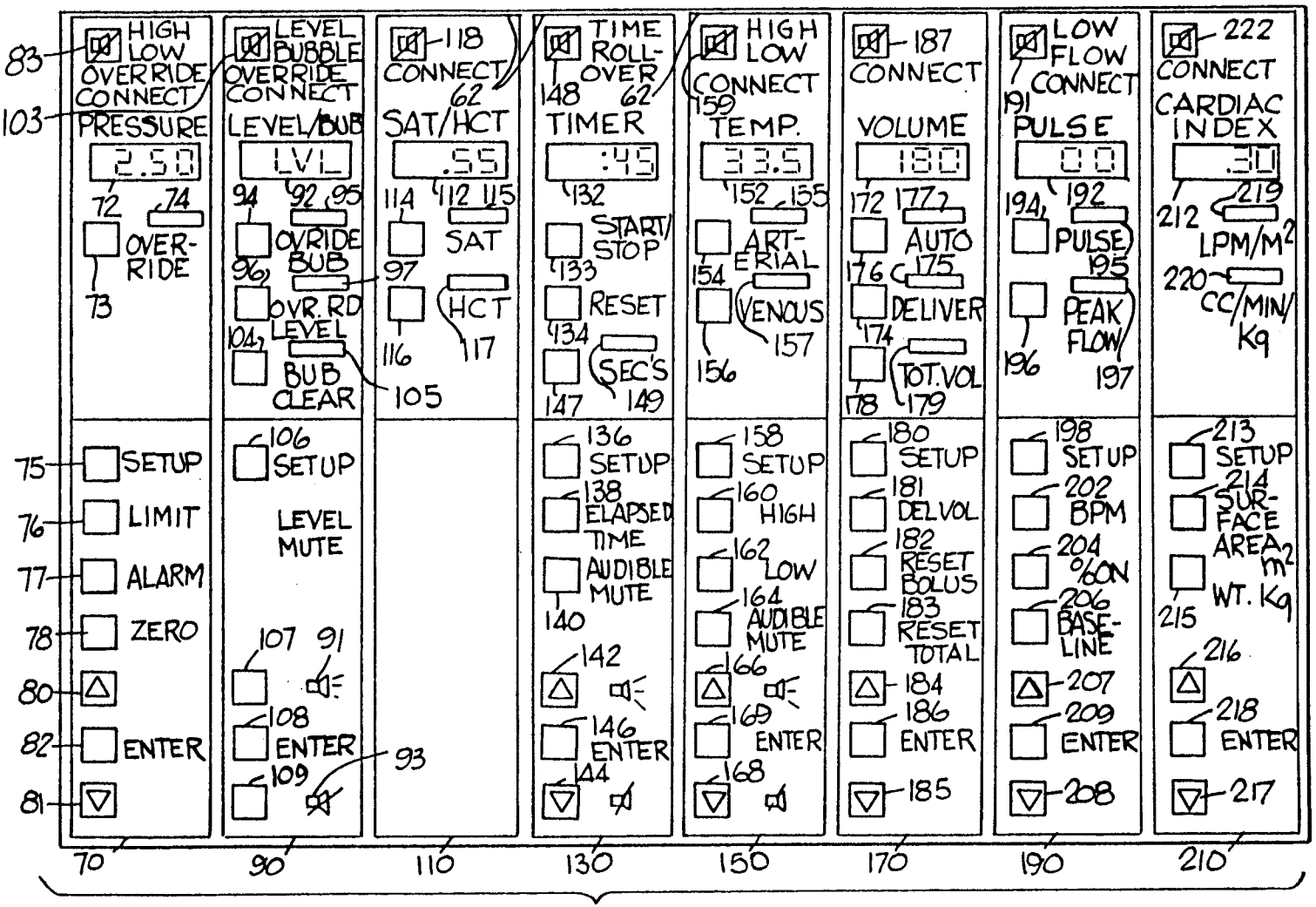
FIG. 4 is a front view of the control module pod instrumentation strips for a perfusion assembly configured as a highly featured arterial perfusion assembly.

Each detachable circuit card 42 in the control module pod 28 is associated with an instrumentation strip 62 in the control module pod. The instrumentation strips are strips of labels to label the buttons of the instrumentation slot to which it is attached, and are referred to generically as "label sets" in the appended claims. FIG. 4 depicts a variety of possible instrumentation strips 62 for a perfusion assembly, including a pressure strip 70, a level/bubble strip 90, a saturation and hematocrit strip 110, a timer strip 130, a temperature strip 150, a volume strip 170, a pulse strip 190 and a cardiac index strip 210. Each instrumentation strip may contain suitable graphics and wording in a desired language to identify the various controls. Although FIG. 4 shows eight different instrumentation strips 62, a given perfusion assembly normally uses much less than eight. Therefore, the preferred embodiments shown in FIGS. 1–3 are designed to accept a maximum of five instrumentation strips 62 on each perfusion assembly 20. For a perfusion assembly used as an arterial perfusion assembly, for example, there might be instrumentation strips 62 for pressure 70, level/bubble 90, saturation and hematocrit 110, timer 130 and temperature 150. Other desired arterial perfusion assemblies might utilize more or less instrumentation strips 62. A perfusion assembly used as a cardioplegia perfusion assembly might have instrumentation strips 62 for pressure 70, level/bubble 90, volume 170, timer 130 and temperature 150. Again, other desired configurations might utilize more or less instrumentation strips as desired. Therefore, the present invention is not intended to be limited to the specific collection or order of instrumentation strips or their functions that are described in detail herein.

Figure 5:
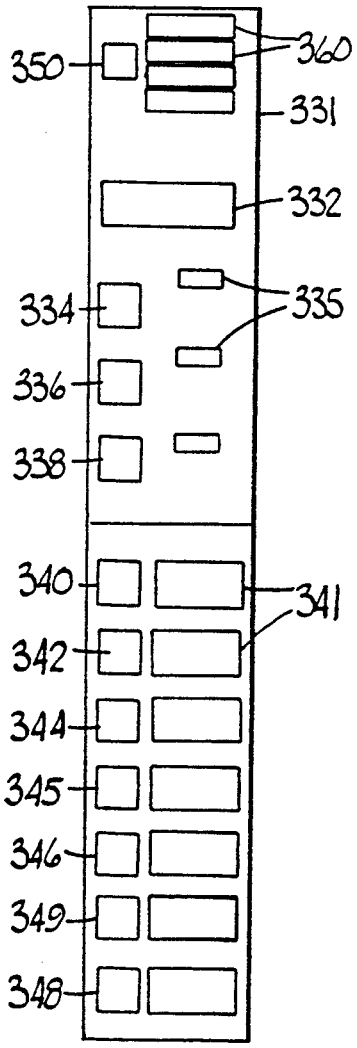
FIG. 5 is a front view of an instrumentation slot of a control module pod.

The control module pod 28 has an instrumentation panel which includes a set of instrumentation slots 331 (five in the preferred embodiment) to receive the individual instrumentation strips 62, as shown in FIG. 5. Each instrumentation slot 331 comprises an instrumentation set which includes all the instrumentation necessary to control and display the functions of any given instrumentation strip 62. However, as explained below, not all of those buttons are actually functional for many of the instrumentation strips 62 that are used. In a preferred embodiment, the instrumentation in an instrumentation slot 331 includes an LED display 332, a set of function buttons 334, 336 and 338, a set of program buttons 340, 342, 344 and 345, a pair of dual purpose adjustment buttons 346 (up and on) and 348 (down and off) located under the function buttons, an enter button 349, and an alarm mute button 350 located above the LED display. Each button may be of the membrane type, so that the button is impermeable to spilled fluids. Because some configurations of a perfusion assembly may employ fewer operating instrumentation strips 62 than there are instrumentation slots 331 in the control module pod 28, any unused instrumentation slots are simply covered with a blank instrumentation strip (not shown). The instrumentation in each instrumentation slot is referred to generically in the appended claims as an "instrumentation set".

In a preferred embodiment, each of the top three function buttons 334, 336 and 338 is accompanied by an indicator light 335, which is displayed through a window in the corresponding instrumentation strip in the manner described below. Each of the bottom four program buttons 340, 342, 344 and 345, as well as the up and down adjustment buttons 346 and 348 and the enter button 349 is also accompanied by a label light 341 which lights the transparent label adjacent and corresponding to that button on the instrumentation strip in the manner described below. Adjacent to the alarm mute button 350 is a set of alarm label lights 360 to light up to four transparent labels adjacent to that button on the instrumentation strip.

The instrumentation strips 62 may be flat flexible strips with suitable labelling for the areas overlying the instrumentation slot 331 buttons. Therefore, the buttons in the instrumentation slots 331 can be activated by applying pressure directly to the overlaying instrumentation strip 62. The labels overlying the label lights of the underlying instrumentation slot 331 are transparent so that those labels light when the label lights themselves light but are essentially invisible when the label lights are not lit. The labels on the instrumentation strips 62 that are permanent labels not overlying label lights on the underlying instrumentation slot 331 are preferably non-transparent so that they are readily visible.

Referring again to FIG. 4, the instrumentation strip 70 for fluid pressure includes an LED window 72 to allow viewing of the LED display 332 from the instrumentation slot 331 of FIG. 5, an Override button 73 with an adjacent override indicator light 74, four program buttons 75, 76, 77, and 78, up and down adjustment buttons 80 and 81 and an Enter button 82. There is also an alarm mute button 83. The LED window 72 is primarily to continuously monitor the pressure of the fluid being pumped, and the other buttons are to enter pressure limits. Adjacent to the alarm mute button 83 are transparent labels for "High", "Low", "Override" and "Connect".

Depending on the relationships of various components of the perfusion system, pressure limit and alarm limit settings may be above or below zero and may alarm on rising or falling pressure. For example, if the pressure limit is set to a value greater than the alarm limit, the pressure and alarm limits will be high limits and will be activated by pressures exceeding the set values. Similarly, if the alarm limit is set to a value greater than the pressure limit, the pressure and alarm limits will be low limits and will be activated by pressures less than the set values.

To enter the pressure limits, the setup button 75 is pressed to make the labels corresponding to the Limit 76, Alarm 77 and Zero 78 buttons flash. Then the Limit button 76 is pressed to light the "Limit" label continuously, to turn off the Alarm and Zero labels and to make the Enter label flash and the display 72 flash the current value of the pressure limit. The up or down adjustment buttons 80 or 81 are pressed to adjust the pressure limit as displayed. When the desired pressure limit is reached by appropriate activation of the up or down adjustment buttons 80 or 81, then the Enter button 82 is pressed to enter that value into the electronic storage of the machine and to exit the setup mode. Once the machine is programmed in this manner, a pressure outside the entered pressure limit will initiate an action as explained below.

A similar procedure is used to enter the alarm limit. The Setup button 75 is pressed to make the Limit, Alarm and Zero labels flash, and the Alarm button 77 is pressed to continuously light the "Alarm" label adjacent to that button and to make the Enter label flash and the display 72 flash the current value of the alarm limit. The adjustment buttons 80 and 81 are used to adjust the displayed values to match desired values, and the display is then entered by pushing the Enter button 82. A pressure outside of the alarm limit will activate the alarm as explained below.

The Zero button 78 is used to calibrate the pressure function. This is done by releasing the pressure on the fluid (such as by opening the fluid to atmospheric pressure), pressing the Setup button 75 and Zero button 78, and then pressing the Enter button 82.

By entering the pressure limits and the alarm limits and calibrating the machine for zero pressure in the manner described above, the pressure strip 70 is ready for operation. Except in the setup mode, the pressure of the pumped fluid is continuously displayed through the LED window 72. If the pressure reaches an alarm limit entered through the Alarm button 77, an audible alarm sounds and the "High" or "Low" label adjacent the Alarm Mute button 83 flashes to indicate whether the pressure is at the upper alarm limit or lower alarm limit. If desired, the audible alarm can be muted by pressing the alarm mute button 83. This also changes the flashing of the "High" or "Low" label to a steady illumination. If the pressure goes even higher (in the case of a pressure exceeding the upper alarm limit) or lower (in the case of a pressure below the lower alarm limit) to the point where the pressure reaches a pressure limit entered through the Limit button 76, then one of two things will happen. In one embodiment, the machine will simply stop pumping. In another embodiment, the pump rate will be automatically increased or decreased to try to bring the pressure within the limit range. In either event, these consequences can be overridden by pressing the Override button 73 to light the adjacent light 74. In that event, the "Override" label adjacent the Alarm Mute button 83 will be lit, the LED display 72 will simply display the pressure, and the machine will not attempt to maintain the pressure within the preset limit range. If a pressure limit or alarm limit is reached while in the setup mode, the setup mode will be exited from automatically and the action described above taken. The setup mode may be reentered by pressing the Setup button 75 and subsequent alarms which occur while in the setup mode will also cause exit from the setup mode.

If communication with a sensor or the pump is lost, such as by interruption of the electrical connection with the pressure sensor, the "Connect" label adjacent the alarm mute button 83 flashes and the audible alarm sounds. The flashing "Connect" label can be changed to steady illumination and the audible alarm can be muted by pressing the alarm mute button 83.

It can be seen that the buttons from the instrumentation slot 331 (see FIG. 5) utilized by the pressure instrumentation strip 70 includes function button 334 and the indicator light 335 adjacent to function button 334, and program buttons 340, 342, 344 and 345, along with their adjacent label lights 341, the adjustment buttons 346 and 348, and the Enter button 349 and its adjacent label 341. It uses the alarm mute button 350 and the four label lights 360 adjacent the alarm mute button 350. It does not use two of the function buttons 336 and 338 or their adjacent indicator lights 335. Those buttons are still present on the instrumentation slot 331, and may be pressed by applying pressure to them through the overlying flexible instrumentation strip 70, but there is no label on the instrumentation strip 70 for the button and so it is not visible on the instrumentation strip 70, and pressing it does nothing because the button is not active in conjunction with the pressure circuit card 42 that is used with the pressure instrumentation strip 70. In other words, it is a "dummy" button when used with the pressure instrumentation strip. However, by including that button along with all the other buttons, the instrumentation slots 331 become modular in a way that not only simplifies manufacturing but also allows the user some flexibility in choosing which instrumentation slot 331 will receive a given instrumentation strip 62.

The level/bubble instrumentation strip 90 shown in FIG. 4 in a preferred embodiment includes an LED window 92 to allow viewing of the LED display and two override buttons 94 and 96 along with corresponding adjacent indicator lights 95 and 97, respectively. The first override button 94 is labelled "Override Bubble". So long as that button is not activated to illuminate the adjacent light 95, the air detector function will stop the pump if a bubble is detected in the fluid in the tubing as determined by an air bubble sensor (not shown) engaged with the tubing. The second override button 96 is labelled "Override Level". So long as that button is not activated to illuminate the adjacent light 97, the level/-bubble function will stop the pump if the fluid level in the reservoir drops below a predetermined level as determined by a sensor mounted on the reservoir. The level/bubble instrumentation strip 90 also includes an alarm mute button 103 and four adjacent labels for "Level", "Bubble", "Override" and "Connect.

When a bubble is detected in the fluid or the fluid in the reservoir drops below a predetermined level, the appropriate label "Level" or "Bubble" flashes adjacent the alarm mute button 103 and the audible alarm sounds. The audible alarm will also sound and the "Connect" label adjacent the alarm mute button 103 will flash for lost communications, such as interruption of the electrical connection with the remote sensor or pump. The audible alarm may be muted by the alarm mute button 103 and then the appropriate label will change from a flashing mode to a steady illumination mode.

The operator may resume the pumping or may prevent the pumping from being stopped, notwithstanding the detection of air in the fluid in the tubing or a low fluid level in the reservoir, by pressing the desired override button: Override Bubble 94 to light the adjacent indicator light 95 or Override Level to light the adjacent indicator light 97. If the Override Bubble button 94 is pressed, then the detection of air in the fluid in the tubing will still illuminate the "Bubble" label adjacent the Alarm Mute button 103 and sound the audible alarm, but it will not stop the pump. Similarly, if the Override Level button 96 is pressed, then the detection of an impermissible low fluid level will still illuminate the "Level" label adjacent the Alarm Mute button 103 and sound the audible alarm but it will not stop the pump. If air is detected in the fluid in the tubing, and the Override Bubble button 94 is not activated, then the pump can resume pumping only by first pressing the Bubble Clear button 104 to light the adjacent indicator light 105 while the button 104 is held.

The alarm for the level detector can be muted at the outset through the program buttons 106, 107, 108 and 109. By pressing the Setup button 106, the nearby "Level Mute" label is illuminated and alarm icons 91 and 93 adjacent to the audible alarm and mute buttons 107 and 109 flash. The operator then press either the audible alarm button 107 or the mute alarm button 109 causing the Enter label adjacent to the Enter button 108 to flash. The operator then enters the choice exits the setup mode by pressing the Enter button 108. In view of the importance of the bubble detection system, the preferred embodiment does not include a provision to mute the audible alarm for bubble detection at the outset.

The LED window 92 in the level/bubble instrumentation strip 90 can be used for diagnostic purposes in determining faults with the system. The LED windows on the other instrumentation strips can be used for similar purposes in addition to the uses described herein.

It can be seen from FIG. 4 that the level/bubble instrumentation strip 90 has a button label for the first function button 334, the second function button 336 and the third function button 338 below the LED display 332 on the instrumentation slot 331. This is in contrast to the pressure instrumentation strip 70 which does not utilize the second or third function button 336 or 338. The level/bubble instrumentation 90 in this embodiment does not utilize program 342, 344 or their associated label lights 341. As in the case of the unused buttons associated with the pressure instrumentation strip 70, those unused buttons are still present on the underlying instrumentation slot 331 as "dummies" and can be pressed by applying pressure to the area of the flexible instrumentation strip 90 overlying the button, but the instrumentation strip 90 has no label to indicate the position of the unused buttons and the buttons are not active with the circuitry.

The saturation and hematocrit instrumentation strip 110 is to the immediate right the level/bubble instrumentation strip 90 in FIG. 4. In the preferred embodiment, the oxygen saturation level and the hematocrit is determined by a sensing unit of the type known in the art (not shown), which positioned remote from the perfusion assembly. It is in communication with a corresponding circuit card 42 plugged into the control module pod 28 in the manner previosly described. The saturation and hematocrit instrument strip includes an LED window 112 to allow viewing of the LED display 332, a Saturation function button 1 (abbreviated "SAT" in FIG. 4) and associated indicator 115 to choose a display of saturation level, and a function button 116 (abbreviated "HCT" in FIG. 4) and associated indicator light 117 to choose a display of hematocrit. If communication with the sensing unit is interrupted, the audible alarm sounds and the "Connect" label adjacent the alarm mute button 118 flashes. Pushing the alarm mute button 118 silences the audible alarm and causes the Connect label to light steadily.

The saturation and hematocrit instrumentation strip is operated by pressing the Saturation button 114 to light the saturation indicator light 115 and to display saturation, or pressing the hematocrit button 116 to light the Hematocrit indicator light 117 and to display the hematocrit of the pumped blood. Initial calibration of the hematocrit sensor is obtained by a separate remote calibration device the type known in the art.

The timer instrumentation strip 130 is immediately to the right of the saturation and hematocrit instrumentation strip 110 in FIG. 4. The timer instrumentation strip 130 includes a LED window 132 to allow viewing of the LED display, a Start/Stop button 133, and a Reset button 134. The LED window 132 normally displays hours and minutes, but can be made to display seconds by pressing the Seconds button 147, which also lights the associated indicator light 149. Program buttons include a Setup button 136, Elapsed Time button 138, Audible Mute button 140, Up/On buttons and Down/-

Off buttons 142 and 144, respectively, and an Enter button 146, all of which have adjacent labels.

The timer instrumentation strip 130 is initially programmed by pressing the Setup button 136 which makes the labels adjacent the Elapsed Time button 138 and Audible Mute button 140 flash. One of those two buttons is then pushed to make the adjacent label be illuminated steadily and to make the other label go off. For example, if the Elapsed Time 138 is pushed, it illuminates the adjacent label steadily and the flashing label adjacent to the Audible Mute button 140 goes off. The amount of time to be programmed is then entered by pressing the up/on and down/off buttons 142 and 144, respectively, to display the desired time through the LED window and then pressing the Enter button 146 to enter that time. The Audible Mute button 140 is operated by pressing it after pressing the Setup button 136, and then pressing either the up/on button 142 and the Enter button 46 for an audible alarm or the down/off button 144 and the Enter button 146 for a muted alarm.

The Start/Stop button 133 is pressed to begin counting time, and that count is displayed on the LED display. When in the stop mode the display may be reset to zero. To reset the display to zero, the Reset button 134 is pressed. If the count is to be temporarily stopped, the Start/Stop button 133 is pressed, and the time until that point is stored and then counting is resumed when the Start/Stop button is pressed yet again. To alert the operator when the counted time reaches the amount programmed through the Elapsed Time button 138, the "Time" label adjacent the Alarm Mute button 148 flashes. If the machine was programmed with an audible alarm through the up/on button 142, the audible alarm also sounds. The audible alarm is silenced, and the flashing "Time" label is changed to continuously lit, by pressing the Alarm Mute button 148. The "Rollover" label adjacent the Alarm Mute button 148 indicates that the displayed time has "rolled over" the entire display capacity and is now counting the second time.

The temperature instrumentation strip 150 is to the immediate right of the timer instrumentation strip 130 in FIG. 4. The temperature instrumentation strip 150 includes an LED display window 152 to allow viewing of the LED display, two function buttons, for Arterial temperature 154 with an adjacent indicator light 155 and for Venous temperature 156 with an adjacent indicator light 157. The function buttons are used to choose the temperature that is displayed on the LED display; the arterial temperature is displayed if the Arterial button 154 is pressed, and the venous temperature is displayed if the Venous button 156 is pressed. The "arterial" temperature refers to the temperature of the fluid at the arterial temperature sensor, which is generally placed near the heat exchanger before the fluid enters the patient. The "venous" temperature refers to the temperature of the fluid at the venous temperature sensor, which is generally placed in the reservoir or tubing upstream from the heat exchanger. Of course, "Arterial" and "Venous" could be replaced with less specific labels such as "Channel 1" and "Channel 2", and may be used to display temperature other than that of the fluid being pumped such as patient rectal or esophageal temperature.

The alarm thresholds for the temperature instrumentation strip are set with the program buttons. To set the threshold for the arterial and venous temperatures, the user presses the Arterial or Venous button 154 or 156, respectively. The Setup button 158 is pressed to illuminate the labels adjacent the High 160, low 162 and Audible Mute 164 buttons in a flashing mode. The desired button of those three is then pressed to light the adjacent label continuously and to switch off the other flashing labels. If the High button 160 is pressed, then the upper limit is entered using the up/on and down/off buttons 166 and 168, respectively, and then the Enter button 169. The lower limit is entered through the Low button 162 using the same process. The alarm can be either audible or inaudible, in the same manner as the alarm on the timer instrumentation strip 130; the Setup button 158 is pressed, the Audible Mute button 164 is pressed, and then either the up/on button 166 (for an audible alarm) or down/off button 168 (for an inaudible alarm) is pressed and the Enter button 169 is pressed.

If the arterial or venous temperature falls outside the preset alarm thresholds, the alarm will be activated, regardless of which temperature is being displayed at that time. In order to indicate whether it is the arterial or venous temperature that is outside the range set, the display of that temperature in the LED display flashes on and off when that temperature is being displayed and the indicator light adjacent to the corresponding channel button 155 and 157 flashes on and off. At the same time, either the "High" or "Low" label adjacent the Alarm Mute button 159 flashes to indicate whether the temperature is too high or too low. If the audible alarm has been set through the Audible Mute button 164 and the up/on button 166, then the audible alarm will sound as well. The audible alarm is muted and the flashing "High" or "Low" label is made steady by pressing the Alarm Mute button 159. The "High" or "Low" label will continue to be lit until the temperature returns to the preset range or the range is adjusted to include that temperature.

The "Connect" label adjacent the Alarm Mute button 159 has the same use as in the other instrumentation strips; if communications with a sensor is interrupted, such as when the electrical connection with the sensor is interrupted, the "Connect" label flashes and the audible alarm sounds. Again, the audible alarm can be muted and the "Connect" label changed from flashing to continuously lit by pressing the Alarm Mute button 159.

The volume instrumentation strip 170 is immediately to the right of the temperature instrumentation strip 150 in FIG. 4. The volume instrumentation strip 170 includes an LED window 172 to allow viewing of the LED display, and three function buttons Deliver 174 and associated indicator light 175, Automatic 176 (abbreviated "Auto" in FIG. 4) and associated indicator light 177 and Total Volume 178 (abbreviated "Total Vol" in FIG. 4) and associated indicator light 179. The program buttons include Setup 180, Delivery Volume 181 (abbreviated "DelVol" in FIG. 4), Reset Bolus 182, Reset Total 183 and Enter 186, and up and down adjustment buttons 184 and 185. The Auto button 176 is pressed and the adjacent indicator light is illuminated when the perfusionist desires the pump to be controlled by the volume instrument strip 170 functions. Pressing the auto button 176 again will turn off the adjacent indicator light 177 and return the pump to manual control. In the Auto mode the Deliver button 174 is pressed to deliver solution and is pressed again to discontinue the delivery of solution. The Auto button 176 is pressed to turn the Auto mode off, for example, when the perfusionist recirculates solution through a heat exchanger under manual pump control to maintain a desired solution temperature. The pump continues to run at this transition.

These buttons are used to monitor and control the volume of delivered solution. By pressing the Deliver button 174, the operator can light the associated indicator light 175 and deliver a volume of solution programmed by the program buttons described below at the flow rate specified in the pump control panel 33. While pressing the Total Vol button 178, the LED display 172 displays the total volume of solution delivered to the patient.

The program buttons include a Setup button 180. By pressing the Setup button 180, the operator flashes the labels adjacent to the Del Vol button 181, the Reset Bolus button 182 and the Reset Total button 183. By pressing the Del Vol button 181, the adjacent label is illuminated steadily, and the operator can choose a desired delivery volume by pressing the up and down adjustment buttons 184 and 185, respectively, and then the Enter button 186. The Reset Bolus button 182 is used to return an accumulated bolus count to a desired delivery volume. For example, if the bolus of solution for delivery is set at 500cc and 200cc have been delivered with another 300cc to go, activating the Reset Bolus button 182 will erase the 200cc already delivered from the delivery count and instruct the machine to deliver 500cc by restarting the counting from 500. The Reset Total button 183 operates in a similar manner; pressing that button and the Enter button 186 will erase the accumulated total volume as displayed by the Total Vol button 178 and begin recounting total volume delivered from zero.

The volume instrumentation strip 170 also includes a "Connect" label adjacent the alarm mute button 187. The "Connect" label flashes, the audible alarm sounds and automatic control of volume delivery is disabled if communication with the pump 24 is interrupted. The "Connect" label can be changed to steady illumination and the audible alarm muted by pressing the alarm mute button 187.

There may be an operative relationship between the volume instrumentation strip 170 and the timer instrumentation strip 130. The machine may be designed so that the timer in the instrumentation strip 130 stops counting when the solution is delivered by the volume instrumentation strip 170, and starts counting when the solution is no longer delivered by the volume instrumentation strip 170. This can be accomplished by, for example, a trip switch (not shown) which automatically ties together the two instrumentation strips 170 and 130 whenever they are positioned side by side.

The pulse instrumentation strip 190 is to the immediate right of the volume instrumentation strip 170 in FIG. 4, and is used to control the pulsation of the pump. It includes an LED window 192 to allow viewing of the LED display, a Pulse button 194 and associated indicator light 195, and a Peak Flow button 196 and associated indicator light 197. If the Pulse button 194 is not activated, then the pump will not pulsate and the flow will instead be continuous. If the Pulse button 194 is activated, then the flow can be made pulsatile in accordance with the pulsation parameters entered through the Program buttons. If the flow is pulsatile, the beats per minute is displayed on the LED display. The peak flow in the pulse, in volume per unit of time can be momentarily displayed by holding down the Peak Flow button 196 which also lights the associated indicator light 197.

The pulsation parameters are set through the Setup button 198. In particular, the beats per minute are set by pressing the Setup button 198 and then the BPM button 202 is used to program the pulsation "beats" per minute. The LED display then displays the beats per minute and the operator can adjust the rate by pressing the up and down buttons 207 and 208. Unlike most of the adjustments in the instrumentation strips, the machine responds immediately to adjustments in the pulsation parameters, in order to allow the operator to make real time modifications. The adjusted values, however, are not entered into non—volatile memory until the Enter button 209 is pressed. The cycle time button 204 (abbreviated "% On" in FIG. 4) is used to program the amount of time the pump is at peak flow rate as a percentage of the total time from the start of one beat to the start of the next beat. This button is operated in the same manner as the BPM button; the Setup button 198 is pressed, the % On button 204 is pressed, the LED display figure is adjusted using the up or down adjustment buttons, and the adjusted figure is entered into non-volatile memory by pressing the Enter button. The Baseline button 206 is used to program the flow rate at the minimum—or "baseline"—pump speed in the pulsation cycle. (A graph of pump speed against time showing the pulsation of the pump would show a series of square waves with a minimum—or "baseline"—pump speed that abruptly changes to a maximum pump speed and then back to the minimum pump speed.) The Baseline button is operated in the same manner as the BPM and Cycle Time buttons; the Setup button 198 is pressed, the Baseline button 206 is pressed, the figure in the LED display 192 is adjusted as desired using the up or down adjustment buttons, and the adjusted figure is entered into non-volatile memory by pressing the Enter button 209.

The peak flow in pulsatile operation is not programmable through the pulse instrumentation strip in the preferred embodiment. This is because the machine automatically computes and establishes the maximum speed based on the beats per minute, cycle time and baseline values programmed into the machine through the pulse instrumentation strip along with the overall flow rate set by the flow dial of the pump control panel 33 in the manner described below. It should be apparent that, if desired, the machine could instead be constructed so that the maximum speed were a programmed value and the baseline speed or some other value were computed from the maximum speed in combination with the other programmed values.

There is an operative relationship between the pulse function as controlled by the pulse instrumentation strip 190 and the pressure function as controlled by the pressure instrumentation strip 70. This is because the maximum pump speed as computed based on the beats per minute, cycle time and baseline as programmed into the machine through the pulse instrumentation strip 190 and the overall flow rate as set by the flow dial (described below), could result in a maximum pressure during the peak flow portion of the pulse that is greater than the maximum permissible pressure entered through the pressure instrument strip 70. If this happens, then the alarm on the pressure instrumentation strip 70 will be activated causing the "High" label adjacent to the alarm mute button 83 to flash. In addition, the pump will be stopped unless the Override button 73 on the pressure instrumentation strip 70 is activated, as described previously.

The alarm on the pulse instrumentation strip 180 is activated if the user attempts to program pulsation parameters that cannot be met by the machine, such as low cycle time and baseline flow parameters that will not achieve the total flow rate previously established. If that happens, the "Low Flow" label adjacent the alarm mute button 191 will flash and the audible alarm will sound. The audible alarm can be muted and the flashing label made steady by pressing the Alarm Mute button 191. In addition, there is a "Connect" label adjacent the alarm mute button 191 which flashes if the communication between the pump 24 and the control module pod 28 is interrupted. Further, loss of communication will disable the pulse mode.

The last instrumentation strip 62 in FIG. 4 is the cardiac index strip 210. It includes an LED window 212 to allow viewing of the LED display, and a set of program buttons for Setup 213, Surface Area 214, Weight 215, up and down adjustment buttons 216 and 217, and an Enter button 218. If the cardiac index is to be computed and displayed based on patient surface area, then the machine is set up by pressing the Setup button 213 and then the Surface Area button 214, and then adjusting the LED display 212 using the up and down adjustment buttons 216 and 218, respectively, until the desired surface area is displayed, and then pressing the Enter button 218. If the cardiac index is to be computed and displayed based on patient weight, then the same procedure is followed except that the Weight button 215 is pressed instead of the Surface Area button 214.

If the cardiac index is computed and displayed based on patient surface area, then the $LPM/m^2$ (for liters per minute per square meter of surface area) indicator light 219 is illuminated. If the cardiac index is computed and displayed based on patient weight, then the cc/min/kg (for cc's per minute per kilogram of weight) indicator light 220 is illuminated. The cardiac index in the chosen method of computation is displayed through the LED window 212.

As in the case of several other instrumentation strips, if the communication between the pump 24 and the control panel pod 28 is interrupted, the audible alarm sounds and the "Connect" label adjacent the Alarm Mute button 222 flashes and the cardiac index function is disabled. The audible alarm can be muted and the adjacent "Connect" label changed to steady illumination by pressing the Alarm Mute button 222.

Figure 6:
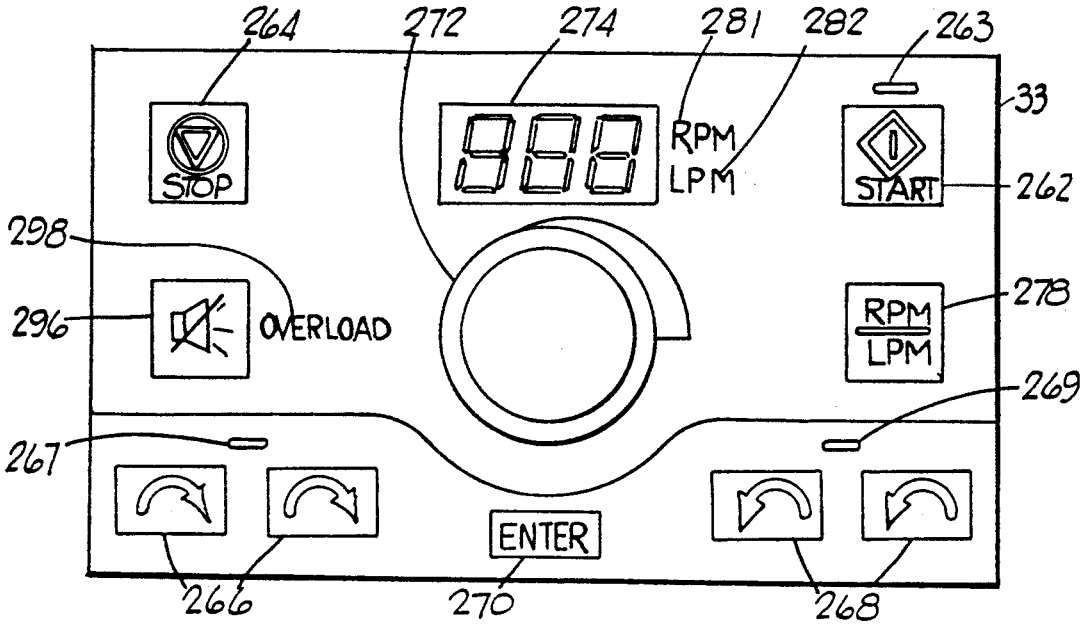
FIG. 6 is a front view of the upper portion of a perfusion assembly, showing the pump control panel.

The pump control panel 33, located on the pump 24 and positioned above the instrumentation slots 331 of the control module pod 28 when the pump 24 is assembled with the control module pod 28, is shown in detail in FIG. 6. The pump control panel 33 may be of the same flexible material as the instrumentation strips 62 and may cover membrane-type buttons of the same design as those on the instrumentation slots 331. Unlike the instrumentation strips 62, the control pump panel 33 is preferably designed to be fixed to the pump housing 30.

The pump control panel 33 instrumentation includes a Start button 262 to operate the pump and an associated indicator light 263 to indicate the pump is on, and a Stop button 264 to stop operation of the pump. A pair of clockwise rotation buttons 266 and counterclockwise rotation buttons 268 are used to cause clockwise or counterclockwise rotation of the pump rotor. Each of the clockwise rotation button 266 and counterclockwise rotation button 268 has an associated indicator light 267 and 269, respectively, to indicate the chosen direction of rotation. The direction of rotation is established by pressing both of the clockwise rotation buttons 266, or both of the counterclockwise rotation buttons 268, simultaneously with the Enter button 270 that is located between the clockwise rotation buttons 266 and counterclockwise rotation buttons 268.

The speed and flow rate is controlled and indicated using a flow dial 272, which is turned clockwise to increase the pump speed and counterclockwise to decrease the pump speed. The pump speed obtained by adjustment of the flow dial 272, in revolutions per minute, is displayed on a flow/speed LED display 274. Alternatively, the flow/speed LED display 274 can be used to display the fluid flow rate in liters per minute. The choice of displaying the pump rotational speed in revolutions per minute or the volume flow rate in liters per minute is made with the RPM/LPM button 278. Pressing that button 278 causes the LED display 274 to display revolutions per minute if it was previously displaying liters per minute, and causes it to display liters per minute if it was previously displaying revolutions per minute. The chosen display is indicated by illuminating either an "RPM" label 281 or an "LPM" label 282 adjacent the flow/speed LED display 274. There may also be another set of controls (not shown) to set the pump for various sizes of tubing so that the machine connected computes flow rates based on measured pump rotational speeds.

The pump control panel 33 also includes an alarm mute button 296 and an Overload indicator light 298. The Overload indicator light 298 flashes when the pump motor draws current at a level that indicates high resistance to the rotation of the pump rotor so that the desired pump speed cannot be attained, such as when the occlusion setting on the rollers is excessive. When the Overload indicator light 298 is lit, the audible alarm also sounds. As in the case of other events triggering an audible alarm, this audible alarm can be muted by pressing the alarm mute button 296, but the Overload indicator light 298 will remain steadily lit until the overload condition is relieved.

Figure 7:
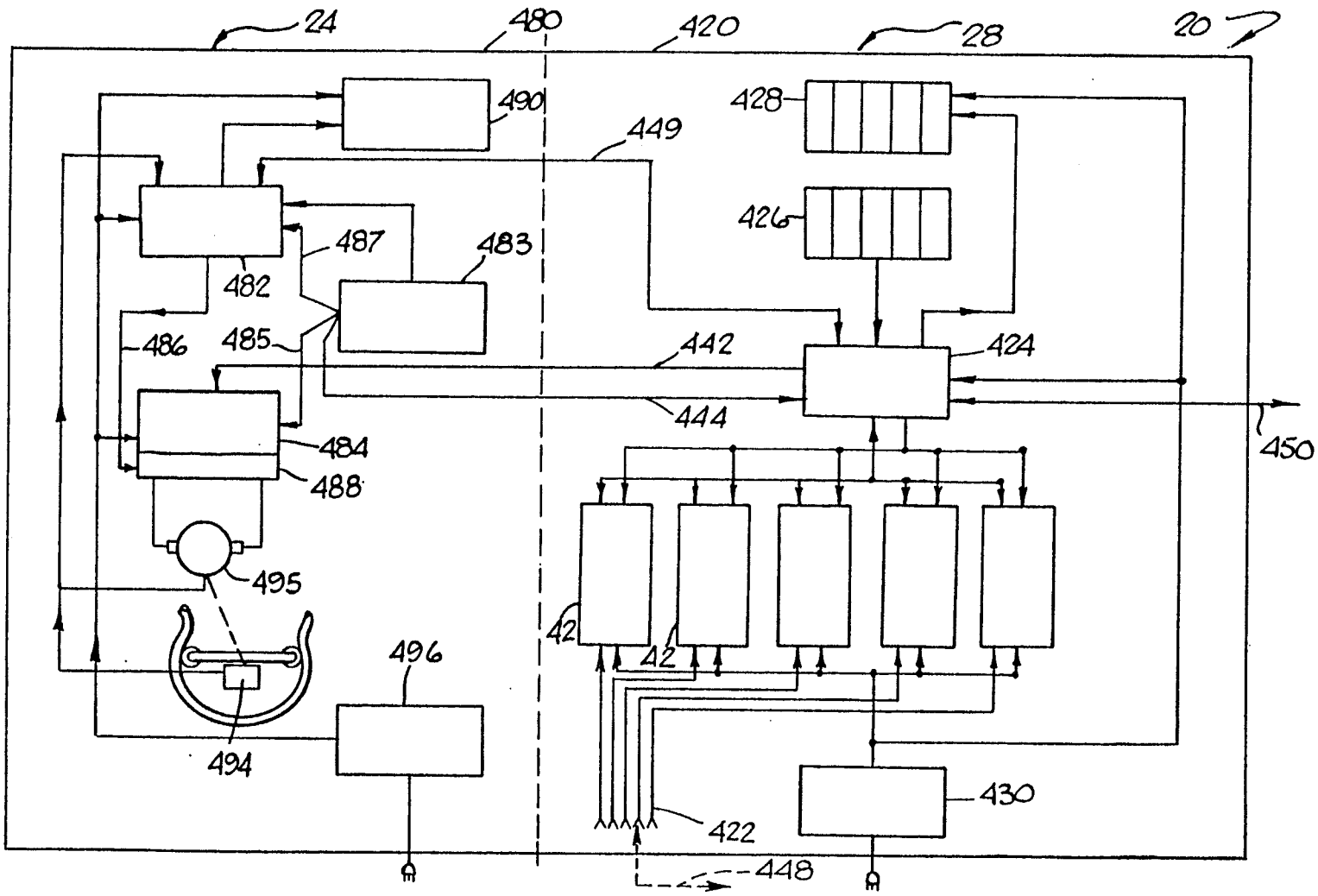
FIG. 7 is a block diagram of the electrical system for a perfusion assembly.

A block diagram of the electrical system for the perfusion assembly 20 is shown in FIG. 7. The electrical system includes a control module pod portion 420 in the control module pod 28 and a pump portion 480 on the pump 24. The control module pod portion 420 has a set of replaceable circuit cards 42 which receive sensor signals from remote sensors (not shown) through a set of sensor inputs 422. The circuit cards are in communication with at least one microprocessor 424. The data input portions 426 of the instrumentation slots 331 (FIG. 5) are connected to the microprocessor 424 to control the input of data. The microprocessor 424 is also in communication with display portions 428 of the instrumentation slots 331 to display the desired data. The circuit cards 42, microprocessor 424, and instrumentation slot display portions 428 are all powered by a power supply 430 for the control module portion 420.

The pump portion 480 of the electrical system includes a pump monitor 482 which is controlled by the control panel instruments 483 that are on the pump control panel 33 (from FIG. 6). Critical control signals are sent from the control panel instruments 483 to the pump control unit 484 by a critical control line 485 and also to the monitor 482 by another critical control line 487. In the event of a malfunction, the monitor 482 will stop the pump through an enable/disenable line 486 in communication with a pump amplifier unit 488. The monitor 482 is connected to the pump display 490 to display the various pumping functions previously described. The display is also connected through the pump monitor 482 to sensors on the pump itself 494 and the motor 495 which determine the rotor speeds. A difference between pump and rotor speeds is indicative of drive slippage or failure. The display 490, monitor 482 and pump control unit 484 are all powered by a power supply 496 which is independent from the power supply 430 used in the control module pod portion 420.

The control module pod portion 420 and the pump portion 480 are connected by command lines 442 in one direction and 444 in the other direction. One set 442 runs from the control module pod portion microprocessor 424 to the pump portion pump control unit 484, and the other set 444 runs from the pump portion control panel 483 back to the control module pod portion microprocessor 424. A serial communication line 450 such as an external RS 232 line may be connected to the control module pod portion microprocessor 424. An inter-module communication line 449 runs from the pump portion monitor 482 to the control module pod portion microprocessor 424. The serial communication line 450 may be used to communicate with medical or computing equipment (not shown) external to the perfusion assembly 20.

Additional mater/slave communication lines 448 may optionally be provided to enable communication between the microprocessor 424 and instrumentation slots 331 and circuit cards 42 installed in a separate control module pod 28 of the system 10. The master/slave communication lines 448 communicate with the microprocessor 424 through a circuit card 42 having field terminals provided for that purpose. When a master/-slave communication line is provided, it expands the number of functions that may be associated with the perfusion assembly 20.

Many functional details of the preferred embodiment of the present invention have been described in detail. It will be appreciated by those skilled in the art that many variations of these functional details are possible without departing from the spirit of the present invention.

We claim:

1. A system controllable by a system operator for extracorporeal pumping of fluids between a pump assembly and a patient, comprising an instrumentation panel for controlling and monitoring at least one of a pumping or a patient parameter, a housing having at least one receptacle adapted to receive at least one selected circuit card removably attached to the receptacle and in electrical communication with the instrumentation panel for processing electrical signals indicative of the parameter, said selected circuit card being selected from a plurality of different circuit cards, each different circuit card having circuitry for the processing of different parameters.

2. The system of claim 1, further comprising said plurality of circuit cards, wherein said plurality of circuit cards are for processing signals indicative of at least one of pressure of the pumped fluid, volume of the pumped fluid, temperature of the pumped fluid, temperature of the patient, the presence of air in the pumped fluid, level of the pumped fluid in a reservoir, the hemoglobin oxygen saturation level of the pumped fluid, the hematocrit of the pumped fluid, the pulsation of the pumped fluid, the time of pumping of the pumped fluid and the cardiac index.

3. The system of claim 1, wherein the system includes a communications port to receive an external communications line to transmit pumping parameter information between the system and a location separate from the system.

4. The system of claim 1, wherein the system includes a pump housing and a detachably attached control module, the control module having said instrumentation panel, and the pump housing having a second instrumentation panel.

5. The system of claim 4, wherein the second instrumentation panel includes controls to start and stop the pumping of fluids and to control and monitor the pumping rate.

6. The system of claim 5, wherein the second instrumentation panel includes controls to control and monitor the pumping rate in both volume of fluid pumped over time and speed of the pump.

7. The system of claim 5, wherein the second instrumentation panel includes controls for turning the pump in a first direction of in a second direction opposite the first direction.

8. The system of claim 5, wherein the system includes said pump assembly, and said pump is a peristaltic pump that receives flexible tubing that is occluded by rollers on a rotor.

9. The system of claim 5, wherein the second instrumentation panel includes an indicator to indicate that the pump is overloaded.

10. The system of claim 5, wherein the second instrumentation panel includes a control for muting an audible alarm.

11. The system of claim 1, wherein the instrumentation panel includes a plurality of instrumentation sets, each instrumentation set having a plurality of switches activatable by the operator, and each circuit card being in electrical communication with an associated instrumentation set for monitoring the at least one parameter.

12. The system of claim 11, wherein the instrumentation panel includes a different set of labels associated with each different circuit card selected by the operator, each label set being detachably attached to an associated instrumentation set to label instrumentation set switches, so that a circuit card and associated instrumentation set and associated label set are used to monitor the parameter.

13. The system of claim 12, wherein the instrumentation sets to which label sets may be detachably attached have substantially the same sets of switches.

14. The system of claim 3, wherein at least one instrumentation set includes at least one alarm light, at least one alpha-numerical display, and a set of at least one control switch.

15. The system of claim 14, wherein a label set and circuit card are for monitoring a level in a fluid reservoir.

16. The system of claim 14, wherein a label set and circuit card are for monitoring the presence of air in the fluid being pumped.

17. The system of claim 14, wherein a label set and circuit card are to monitor the hemoglobin oxygen saturation level of the fluid being pumped.

18. The system of claim 14, wherein a label set and circuit card are to monitor the hematocrit of the fluid being pumped.

19. The system of claim 14, wherein a label set and circuit card are to monitor the cardiac index of the patient.

20. The system of claim 14, wherein a label set and circuit card are to monitor time.

21. The system of claim 20, wherein the label set includes labelling for at least one instrumentation set switch for programming an amount of time, after the elapse of which an alarm light is activated.

22. The system of claim 14, wherein a label set and circuit card are to monitor temperature.

23. The system of claim 22, wherein the temperature being monitored is at least one of rectal temperature of the patient, esophageal temperature of the patient and temperature of the fluid being pumped.

24. The system of claim 22, wherein the label set includes labelling for at least one instrumentation set switch to program an upper temperature limit and a lower temperature limit, whereby an alarm light is activated if the monitored temperature is outside of the range between the lower and upper limit.

25. The system of claim 14, wherein a label set and circuit card are to monitor the volume of fluid that is pumped.

26. The system of claim 25, wherein the label set includes labelling for at least one instrumentation set switch to program a volume of fluid to be pumped.

27. The system of claim 25, wherein the label set includes labelling for at least one instrumentation set switch to monitor the total volume of fluid pumped.

28. The system of claim 14, wherein a label set and circuit card are monitoring the pressure of the fluid being pumped.

29. The system of claim 28, wherein the label set includes a labelling for at least one instrumentation set switch to program at least one of an upper pressure limit and a lower pressure limit, whereby an alarm light is activated if the pressure is at least one of below the lower pressure limit or above the upper pressure limit.

30. The system of claim 29, further comprising means for automatically adjusting the pump rate to maintain the fluid pressure at least one of above the lower pressure limit or below the upper pressure limit.

31. The system of claim 30, wherein the instrumentation sets include a control for preventing the automatic adjustment means from automatically adjusting the pump rate to maintain the fluid pressure at least one of above the lower pressure limit or below the upper pressure limit.

32. The system of claim 14, wherein a label set and circuit card are to monitor and control the pulsation of the fluid being pumped.

33. The system of claim 32, wherein the label set includes labelling for at least one instrumentation set switch to cause pulsation of the fluid being pumped.

34. The system of claim 33, wherein the label set includes labelling for at least one instrumentation set switch to program at least one pulsation parameter.

35. The system of claim 34, wherein the label set includes labelling for at least one instrumentation set switch to program pulsation beats per minute.

36. A method for extracorporeal pumping of fluids between a pump assembly and a patient, using a pump assembly, comprising selecting at least one pumping parameter for monitoring from a plurality of pumping parameters that can be monitored, each pumping parameter that can be monitored being associated with a circuit card to process signals indicative of said pumping parameter, removable attaching the circuit card associated with each selected pumping parameter to the pump assembly by placing it into one of a plurality of circuit card receptacles in the pump assembly, and operating the pump assembly to pump fluids while monitoring the selected pump parameters.

37. The method of claim 36, wherein the pump assembly includes a monitor for monitoring said pump parameters, the monitor including a plurality of control sets so that each circuit card associated with a selected pump parameter is associated with a control set for monitoring said pump parameter.

38. The method of claim 37, wherein at least two of the instrumentation sets are substantially the same and each selected pump parameter and associated circuit card and associated control set is associated with a label set with identifies controls on the instrumentation set to monitor the selected pump parameter.

39. The method of claim 38, wherein the selected pump parameters include the presence of air in the fluid being pumped, and the instrumentation set associated with the presence of air in the fluid being pumped includes an alarm to indicate such presence.

40. The method of claim 38, wherein the selected pump parameters include the hemoglobin oxygen saturation level of the fluid being pumped.

41. The method of claim 38, wherein the selected pump parameters include the hematocrit of the fluid being pumped, and the set of controls associated with the hematocrit include a display to display the hematocrit as measured by a sensor.

42. The method of claim 38, wherein the selected pump parameters include the pulsation of the fluid being pumped, and the instrumentation set associated with the pulsation of the fluid being pumped include a set of controls to choose whether the pumping is pulsed or not pulsed, and controls for programming pulsation parameters including pulsation beats per minute.

43. The method of claim 38, wherein the selected pump parameters includes the time of pumping, and the instrumentation set associated with the time of pumping includes a set of controls for programming a measurement of elapsed pump time.

44. The method of claim 38, wherein the selected pump parameters include whether the fluid level in a fluid reservoir is below a predetermined level, and the instrumentation set associated with the level includes an alarm to indicate that the fluid level has dropped below said predetermined level.

45. The method of claim 38, wherein the instrumentation set includes a display of the cardiac index.

46. The method of claim 38, wherein the selected pump parameters include measured temperature and the instrumentation set associated with temperature include a display of the temperature and a set of controls to choose an upper temperature limit and a lower temperature limit and an alarm to indicate that the temperature is outside the range between the upper and lower limits.

47. The method of claim 46, wherein said choosing controls includes an up button to increase the displayed temperature, a down button to decrease the display temperature and an enter button to choose the displayed value as a limit.

48. The method of claim 38, wherein the selected pump parameters include the volume of fluid pumped, and the instrumentation set associated with the volume of fluid pumped includes a display of volume and a set of controls to choose the volume to be pumped.

49. The method of claim 48, wherein the choosing controls includes an up button to increase the displayed volume, a down button to decrease the displayed volume and an enter button to choose the displayed volume as the volume to be pumped.

50. The method of claim 38, wherein the pump assembly includes a second instrumentation panel, and further comprising controlling the pump rate through the second instrumentation panel utilizing a pump rate display and a pump rate adjustment control.

51. The method of claim 50, wherein the second instrumentation panel includes controls for selecting the size of tubing used in a peristaltic pump in the pump assembly and controls for choosing the direction of fluid flow.

52. The method of claim 38, wherein the selected pump parameters include the pressure of the fluid being pumped, and the instrumentation set associated with the pressure of the fluid being pumped includes a display of fluid pressure, a set of controls to choose a pressure limit and an alarm to indicate if the pressure is a preselected one of above or below the pressure limit.

53. The method of claim 52, wherein said choosing controls includes an up button to increase the displayed pressure, a down button to decrease the displayed pressure and an enter button to choose the displayed value as a limit.

54. The method of claim 52, wherein the pump assembly includes means for automatically adjusting the pump rae to maintain the fluid pressure a preselected one of below the chosen upper pressure limit or above the chosen lower pressure limit.

55. The method of claim 54, wherein the instrumentation set includes a control for preventing the automatic adjustment means from automatically adjusting the pump rate to maintain the fluid pressure the preselected one of the above or below the chosen pressure limit.

* * * * *